United States Patent [19]

Langstein et al.

[11] Patent Number: 5,703,182
[45] Date of Patent: Dec. 30, 1997

[54] PROCESS FOR THE PRODUCTION OF POLYISOOLEFINS BY MEANS OF NOVEL METALLOCENE TYPE INITIATOR SYSTEMS

[75] Inventors: Gerhard Langstein, Kürten, Germany; Manfred Bochmann, Norwich; David M. Dawson, Buckinghamshire, both of Great Britain

[73] Assignee: Bayer AG, Leverkusen, Germany

[21] Appl. No.: 789,466

[22] Filed: Jan. 27, 1997

[30] Foreign Application Priority Data

Jan. 31, 1996 [DE] Germany .................. 196 03 331.4

[51] Int. Cl.[6] .................. C08F 4/52; C08F 10/10
[52] U.S. Cl. .................. 526/185; 526/183; 526/348.7; 502/152
[58] Field of Search .................. 526/132, 133, 526/160, 185, 348.7; 502/152, 202

[56] References Cited

U.S. PATENT DOCUMENTS

| | | | |
|---|---|---|---|
| 3,009,972 | 11/1961 | Johnson | 502/152 X |
| 3,376,331 | 4/1968 | Kroll | 526/185 X |
| 4,210,737 | 7/1980 | Kennedy et al. | 526/185 |
| 5,448,001 | 9/1995 | Baird | 526/348.7 X |
| 5,506,316 | 4/1996 | Shaffer | 526/185 |

OTHER PUBLICATIONS

E. Fisher, "Synthesis and Structural Characterization of . . . Compound, Organometallics", 1994, pp. 3324–3329.

Fisher et al., "Synthesis and Structural Characterization of . . . aluminum Alkyl Compounds", 1994, vol. 13.

*Primary Examiner*—Fred Teskin
*Attorney, Agent, or Firm*—Connolly and Hutz

[57] ABSTRACT

Polyisoolefins are produced using the process according to the invention by polymerising isoolefins, optionally with conjugated or unconjugated dienes and/or cationically polymerisable, mono- or polyunsaturated compounds in solution, in suspension or in the gas phase at temperatures of −100° C. to +200° C. and pressures of 0.1 to 100 bar in the presence of an initiator system consisting of aluminium-cyclopentadienyl compounds and boron compounds.

9 Claims, No Drawings

PROCESS FOR THE PRODUCTION OF POLYISOOLEFINS BY MEANS OF NOVEL METALLOCENE TYPE INITIATOR SYSTEMS

The present invention relates to a process for the production of polyisoolefins by solution, suspension or gas phase polymerisation of isoolefins, optionally in the presence of conjugated or unconjugated dienes and/or cationically polymerisable, mono- or polyunsaturated compounds, in the presence of novel initiator systems. The present invention moreover relates to novel initiator systems for the polymerisation of isoolefins.

Cationic polymerisation of isoolefins, most particularly of isobutene, has long been known and is described in numerous publications (c.f., for example, J. P. Kennedy, E. Marechal, *Carbocationic Polymerization*, 1982, A. Gandini and H. Cheradame in *Advances in Polymer Science*, volume 34/35 (1980)). In the prior art, Lewis acids or protonic acids are used as the polymerisation initiators. Polymerisation is preferably performed in the presence of halogenated hydrocarbons, such as methyl chloride, methylene chloride or carbon tetrachloride.

Known processes suffer the disadvantages that, frequently, only low molecular weight polymers are obtained and polymerisation may be performed successfully only at low temperatures in polar, in particular halogenated, solvents. U.S. Pat. No. 5,448,001 discloses a novel metallocene type initiator for the polymerisation of isobutenes. The novel initiator system is intended in particular to be suitable for the production of butyl rubber. A disadvantage of the metallocene type initiator system described in the stated US patent is the elevated production cost of the transitional metal compounds described therein.

The object of the present invention is thus to provide a polymerisation initiator which may be produced more economically, with which isoolefins may be homo- or copolymerised to yield high molecular weight products.

It has now been found that high molecular weight polyisoolefins may be produced at elevated temperatures if the isoolefins are polymerised in the presence of an initiator system based on an aluminiumcyclopentadienyl compound and a boron compound.

The present invention accordingly provides a process for the production of polyisoolefins, which is characterised in that isoolefins of the formula $CH_2=CR^1R^2$, where $R^1$ means methyl and $R^2$ means $C_1–C_{10}$alkyl or $C_3–C_{10}$cycloalkyl, optionally together with conjugated or unconjugated dienes having 4 to 20 carbon atoms and/or cationically polymerisable, mono- or polyunsaturated compounds having 4 to 20 carbon atoms, are polymerised in solution, in suspension or in the gas phase at temperatures of −100° C. to +200° C. and pressures of 0.1 to 100 bar in the presence of initiator systems consisting of the following components:

A) $Cp'_2AlR^3$ and
B) $BR^4R^5R^6$, in which
Cp' is an optionally substituted cyclopentadienyl residue,
$R^3$ denotes $C_1–C_{10}$alkyl or $C_3–C_{10}$cycloalkyl and
$R^4$, $R^5$ and $R^6$ have the meaning of $R^3$ or represent $C_6–C_{18}$aryl groups, which may be mono- or polysubstituted by halogen.

The isoolefins used are preferably those in which $R^1$=methyl and $R^2=C_1–C_6$alkyl, such as methyl, ethyl and propyl. Isobutene and 2-methyl-1-butene, in particular isobutene, are particularly preferred. Preferred conjugated or unconjugated dienes are those having 4 to 10, in particular 4 to 6 carbon atoms, such as butadiene, isoprene, piperylene, 2,3-dimethylbutadiene, 2,4-dimethyl-1,3-pentadiene, cyclopentadiene, methylcyclopentadiene, limonene, myrcene and 1,3-cyclohexadiene, preferably isoprene, piperylene and 2,3-dimethylbutadiene, in particular isoprene.

Further copolymerisable mono- or polyunsaturated organic compounds preferably having 4 to 10 carbon atoms which are suitable for the process according to the invention are styrene, p-methylstyrene and divinylbenzene, particularly preferably divinylbenzene.

In the process according to the invention, the conjugated or unconjugated dienes and/or the mono- or polyunsaturated, organic compounds are incorporated by polymerisation in quantities of 0.01 to 20 mol. %, preferably in quantities of 1 to 10 mol. %, wherein the dienes and the polyunsaturated organic compounds may be incorporated by polymerisation in any mixing ratio relative to each other.

The polymerisation according to the invention is performed in a known manner in solution, suspension or in the gas phase, continuously or discontinuously, in a single stage or in multiple stages, at a temperature of −100° C. to +200° C., preferably of −100° C. to +100° C., in particular of −50° C. to +50° C., and at a pressure of 0.1 to 100 bar, preferably of 1 to 50 bar.

In this polymerisation, initiator component A) is used at a concentration of $10^{-3}$ to $10^{-7}$, preferably of $10^{-4}$ to $10^{-6}$ mol/l of reactor volume.

Initiator component B) is used in a molar ratio relative to component A) of 1:100 to $10^4$:1, preferably of 1:10 to $10^2$:1, most preferably of 1:1 to 10:1 (component B):component A)).

Optionally substituted cyclopentadienyl residues Cp' of component A) which may in particular be considered are those of the following formula:

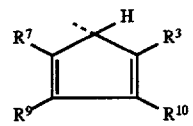

in which $R^7$ to $R^{10}$ are identical or different and denote hydrogen, $C_1–C_{10}$alkyl, $C_3–C_7$cycloalkyl, which may optionally be $C_1–C_{10}$alkyl substituted, $C_6–C_{15}$aryl or arylalkyl or $Si(R^{11})_3$, where $R^{11}$ means $C_1–C_{10}$alkyl, very particularly preferably where $R^{11}$ means methyl.

The methyl residue may in particular be considered as residues $R^7$ to $R^{10}$ of the cyclopentadienyl residues.

Residues $R^3$ of component A) which may be cited are: methyl, ethyl, propyl, butyl, pentyl, hexyl, octyl, nonyl together with decyl and the isomers thereof, preferably methyl, ethyl, n-propyl, isopropyl.

In particular, $(Cp)_2Al(CH_3)$ are used as component A) of the initiator system.

Boron compounds which may be considered as component B) are in particular those in which $R^4$, $R^5$ and $R^6$ denote $C_6F_5$, $CF_3$-substituted aryl residues may also be considered, such as

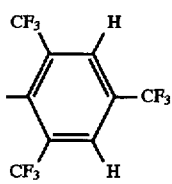

The initiator components may be added to the monomer mixture simultaneously or in succession, continuously or discontinuously. The initiator components may also be preformed. Preforming is taken to mean ageing the initiator components in the absence of the monomers to be used.

The polymerisation according to the invention is preferably performed in solution or suspension. Solvents or suspending agents which may be considered are those organic solvents or suspending agents which are inert under the reaction conditions, such as hexane, isopentane and/or toluene, preferably hexane. It is also possible to use chlorinated hydrocarbons, such as methylene chloride.

The most favourable quantity of solvent and/or suspending agent may readily be determined by appropriate preliminary testing. This quantity is generally 80 to 95 vol. %, relative to the sum of solvent or suspending agent and monomer.

The process according to the invention may, for example, be performed as follows:

The reactor, which has been cooled to the reaction temperature, is charged, for example, with purified solvent and the monomers. Once the reactor has been adjusted to the desired reaction temperature, a small proportion of initiator component B) is apportioned and stirred with the monomer mixture. Initiator component A) and the remainder of initiator component B) are then apportioned and the contents of the reactor vigorously stirred. All handling is performed under protective gas. Once the exothermic reaction is complete, the reaction is terminated, for example, with 2,6-di-tert.-butyl-4-methylphenol, dissolved in ethanol. The reactor is then depressurised, the resultant solution of the polymer is worked up in the usual manner by stripping or, if desired, halogenated in a subsequent reaction. It is possible in this manner directly to functionalise, i.e. halogenate, the resultant polymer.

The present invention also provides a novel initiator system for the polymerisation of isoolefins consisting of
A) $Cp'_2AlR^3$ and
B) $BR^4R^5R^6$,
in which
Cp' is an optionally substituted cyclopentadienyl residue,
$R^3$ denotes $C_1$–$C_{10}$alkyl or $C_3$–$C_{10}$cycloalkyl and
$R^4$, $R^5$ and $R^6$ have the meaning of $R^3$ or represent $C_6$–$C_{18}$aryl groups, which may be mono- or polysubstituted by halogen.

Component A) of the novel initiator system is known, for example, from J. D. Fischer et al., *Organometallics*, 13 (1994), 3324.

Component B) is known, for example, from U.S. Pat. No. 5,448,001.

The polyisoolefins produced using the process according to the invention have average molecular weights $\bar{M}_w$ of 2 to 20000 kg/mol, preferably of 20 to 10000 kg/mol, most preferably of 200 to 800 kg/mol. Yields are generally above 90% of theoretical and were determined gravimetrically.

EXAMPLES

General Description of the Polymerisation Tests

Polymerisation is performed in a glass reactor. To this end, 10 ml of isobutene were condensed in the reactor. To this were added 50 μmol of initiator component B) in 1 ml of solvent (see Table 1). After 1 minute's stirring, the mixture was combined with 50 μmol of initiator component A) dissolved in 0.5 ml of solvent. Polymerisation occurred instantaneously. The reaction was terminated with 0.5 ml of methanol, the polymer precipitated and dried at +60° C. For copolymerisation tests, 0.5 ml of isoprene were additionally added.

Production of the Initiator 1.2 g (2.3 mmol) of $(C_6F_5)_3B$ (=component B)) were added at −78° C. to a solution of 400 mg of $Cp_2Al(CH_3)$ (2.3 mmol) (=component A)), in 10 ml of dichloro-methane. The mixture was stirred for 15 minutes and the solution heated to 0° C., while the solvent was simultaneously removed under a vacuum. The white, solid residue was washed with pentane and dried. 1.6 g of $[Cp_2Al][B(C_6F_5)_3CH_3]$ were obtained (2.3 mmol. 99% yield).

Elemental analysis:

$^1$H—NMR ($CD_2Cl_2$, −60° C.): δ0.55 (s, 3H, Me—B), 705 (s, 10H, Cp).

$^{13}$C—NNR ($CD_2Cl_2$, −60° C.): δ10.5 (s, Br, Me—B), 114.5 (s, CP).

$^{27}$Al—NMR ($CD_2Cl_2$, −20° C.): δ−129.35; (toluene $d_8$): δ−127.4, approx. 55

Polymerisation Examples

TABLE 1

| Test | Comp. A (μmol) | Comp. B (μmol) | Temp. (°C.) | Time (min) | Yield (5) | $\bar{M}_w$ (kg/mol) | $\bar{M}_w/\bar{M}_n$ |
|---|---|---|---|---|---|---|---|
| 1$^a$ | 40 | 40 | −78 | 10 | 0.63 | 731 | 3.0 |
| 2$^b$ | 38 | 38 | −78 | 10 | 0.28 | 1340 | 3.0 |
| 3 | 50 | 50 | −70 | 10 | 0.30 | 1800 | 2.8 |
| 4 | 100 | 50 | −70 | 10 | 0.02 | 820 | 3.4 |
| 5 | 50 | 50 | −50 | 10 | 0.18 | 618 | 2.0 |
| 6 | 50 | 50 | −50 | 10 | 0.08 | 318 | 1.8 |
| 7 | 50 | 100 | −30 | 10 | 0.03 | 337 | 1.8 |
| 8 | 50 | 50 | −25 | 10 | 0.05 | 289 | 1.6 |

Tests 3 to 8: solvent: 1.5 ml of dichloromethane;
$^a$toluene,
$^b$methylcyclohexane

We claim:
1. Process for the production of polyisoolefins, comprising the step of polymerizing isoolefins of the formula $CH_2=CR^1R^2$, where $R^1$ means methyl and $R^2$ means $C_1$–$C_{10}$alkyl or $C_3$–$C_{10}$cycloalkyl, optionally together with conjugated or unconjugated dienes having 4 to 20 carbon atoms and/or cationically polymerisable, mono- or polyunsaturated compounds having 4 to 20 carbon atoms, in solution, in suspension or in the gas phase at temperatures of −100° C. to +200° C. and pressures of 0.1 to 100 bar in the presence of initiator systems consisting of the following components:

A) $Cp'_2AlR^3$ and
B) $BR^4R^5R^6$,
in which
Cp' is an optionally substituted cyclopentadienyl residue,
$R^3$ denotes $C_1$–$C_{10}$alkyl or $C_3$–$C_{10}$cycloalkyl and
$R^4$, $R^5$ and $R^6$ have the meaning of $R^3$ or represent $C_6$–$C_{18}$aryl groups which may be mono- or polysubstituted by halogen.

2. Novel initiator systems for the polymerisation of isoolefins consisting of:
A) $Cp'_2AlR^3$ and
B) $BR^4R^5R^6$, in which
- Cp' is an optionally substituted cyclopentadienyl residue,
- $R^3$ denotes $C_1$–$C_{10}$alkyl or $C_3$–$C_{10}$cycloalkyl and
- $R^4$, $R^5$ and $R^6$ have the meaning of $R^3$ or represent $C_6$–$C_{18}$aryl groups, which may be mono- or polysubstituted by halogen.

3. The process of claim 1 wherein $R^2$=$C_1$–$C_6$alkyl, and the conjugated or unconjugated dienes have 4 to 10 carbon atoms.

4. The process of claim 1 wherein the conjugated or unconjugated dienes and/or the mono- or polyunsaturated, organic compounds are incorporated by polymerization in quantities of 0.01 to 20 mol %.

5. The process of claim 1 wherein the polymerization is conducted continuously, discontinuously, in a single stage or multiple stages.

6. The process of claim 1 wherein the polymerization is conducted at temperatures of $-100°$ C. to $100°$ C. and pressures of 1 to 50 bar.

7. The process of claim 1 wherein initiator component A) is used at a concentration of $10^{-3}$ to $10^{-7}$ mol/l of reactor volume.

8. The process of claim 1 wherein initiator component B) is used in a molar ratio relative to component A) of 1:100 to $10^4$:1.

9. The process of claim 1 wherein initiator component A) is used at a concentration of $10^{-4}$ to $10^{-6}$ mol/l of reactor volume, and initiator B) is used in a molar ratio relative to component A) of 1:10 to $10^2$:1.

* * * * *